(12) United States Patent
Sablone et al.

(10) Patent No.: US 12,364,627 B2
(45) Date of Patent: Jul. 22, 2025

(54) METHOD FOR PRODUCING ABSORBENT SANITARY ARTICLES WITH SIDE PANELS (71) Applicant: Fameccanica.Data S.p.A., San Giovanni Teatino (IT)

(72) Inventors: Gabriele Sablone, San Giovanni Teatino (IT); Antonio Giansante, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 152 days.

(21) Appl. No.: 18/303,660

(22) Filed: Apr. 20, 2023

(65) Prior Publication Data
US 2023/0338199 A1 Oct. 26, 2023

(30) Foreign Application Priority Data
Apr. 22, 2022 (IT) .................. 102022000007979

(51) Int. Cl.
*A61F 13/15* (2006.01)
*A61F 13/494* (2006.01)

(52) U.S. Cl.
CPC .. *A61F 13/15756* (2013.01); *A61F 13/15723* (2013.01); *A61F 13/15747* (2013.01); *A61F 13/4942* (2013.01)

(58) Field of Classification Search
CPC .......... A61F 13/15756; A61F 13/15723; A61F 13/15747; A61F 13/4942; A61F 13/58; A61F 13/15585; A61F 13/15699; A61F 2013/586
USPC ..................................... 604/385.04
See application file for complete search history.

(56) References Cited

U.S. PATENT DOCUMENTS

| 9,301,882 B2 | 4/2016 | Sablone |
| 2008/0319412 A1 | 12/2008 | Lornell |
| 2015/0202091 A1 | 7/2015 | Sablone |
| 2019/0365582 A1 | 12/2019 | Norén et al. |

FOREIGN PATENT DOCUMENTS

| EP | 1269949 A2 | 1/2003 |
| EP | 1941853 A1 | 7/2008 |
| WO | 2011018167 A1 | 2/2011 |

OTHER PUBLICATIONS

Search Report dated Dec. 13, 2022. 7 pages.

*Primary Examiner* — John L Goff, II
(74) *Attorney, Agent, or Firm* — RMCK Law Group PLC (57) ABSTRACT

A method for producing absorbent sanitary articles having a central body, first and second side panels extending laterally outwardly of the central body, and at least one extension band having a distal edge to which at least one closing element is fixed.

6 Claims, 6 Drawing Sheets

METHOD FOR PRODUCING ABSORBENT SANITARY ARTICLES WITH SIDE PANELS

CROSS-REFERENCE TO RELATED APPLICATION

This application claims priority to Italian Patent Application No. 102022000007979 filed Apr. 22, 2022. The disclosure of the above application is incorporated herein by reference in its entirety.

FIELD OF THE INVENTION

The present invention relates to a method for producing absorbent sanitary articles.

In particular, the invention relates to a method for producing absorbent sanitary articles comprising a central body and at least one pair of side panels fixed to at least one end region of the central body.

The invention was developed in particular with a view of producing absorbent sanitary articles for incontinent adults, in particular, for persons suffering from obesity.

Technological Background

Absorbent sanitary articles for incontinent adults generally comprise a central body or chassis with a rectangular shape elongated in a longitudinal direction and having a rear waist section, a front waist section and a crotch section extending between the rear waist section and the front waist section. The central body usually comprises an absorbent core sandwiched between a liquid-permeable topsheet which faces the wearer's skin in use, and a liquid-impermeable backsheet which faces the wearer's clothing in use. The central body may include an acquisition and distribution layer arranged between the topsheet and the absorbent core. The central body may also comprise a pair of elastic leg cuffs, which extend along the topsheet in a longitudinal direction, and which adhere to the user's legs in use.

Absorbent sanitary articles for incontinent adults generally comprise a pair of rear side panels and, optionally, a pair of front side panels. The rear side panels and, if provided, the front side panels have respective proximal sides fixed to corresponding side edges of the rear or front section of the central body and in the condition of use they extend laterally outwards with respect to the central body. The side panels are generally provided at the respective distal ends with closing elements for closing the sanitary article around the user's waist. The side panels may have inclined sides to conform to the user's legs. For example, the side panels may have a trapezoidal shape as described in EP-A-1941853.

Absorbent sanitary articles for obese adults are typically very large in size. For example, the central body may have a length of about one meter and a width of about 90 cm, so that the circumference of the waistband may reach dimensions in the order of 180 cm and above. In these cases, the side panels may have dimensions in the transversal direction that can reach 30-40 cm for each panel.

The large dimensions of the side panels pose various problems both from the point of view of the costs of the raw material, and from the point of view of the production methods.

US20150202091A by the same applicant describes a method for producing absorbent sanitary articles wherein the side panels are partially overlapped and joined together in a provisional manner, and are fixed to two side topsheet webs that are subsequently joined to a central topsheet web.

EP1269949A describes a method for producing absorbent articles provided with side panels, which envisages longitudinally folding a continuous web in a generally Z-shaped configuration, separating single folded side panels from said Z-folded continuous web and attaching the folded side panels at predetermined intervals on a chassis tape.

OBJECT AND SUMMARY

In the state of the art there remains the need to provide absorbent sanitary articles with large side panels, which have lower costs of the raw material necessary for producing the side panels, and which can be produced with more efficient and economical equipment and production processes.

The object of the present invention is to provide a method for producing absorbent sanitary articles that satisfies the aforesaid need, and that solves the problems of the prior art.

According to the present invention, this object is achieved by a method for producing absorbent sanitary articles having the characteristics set forth in one or more of the claims.

Preferred embodiments of the invention form the subject of the dependent claims.

The claims form an integral part of the technical disclosure provided in relation to the invention.

BRIEF DESCRIPTION OF THE DRAWINGS

The invention will now be described with reference to the attached drawings, given purely by way of non-limiting example, wherein.

DETAILED DESCRIPTION

Figure 1:
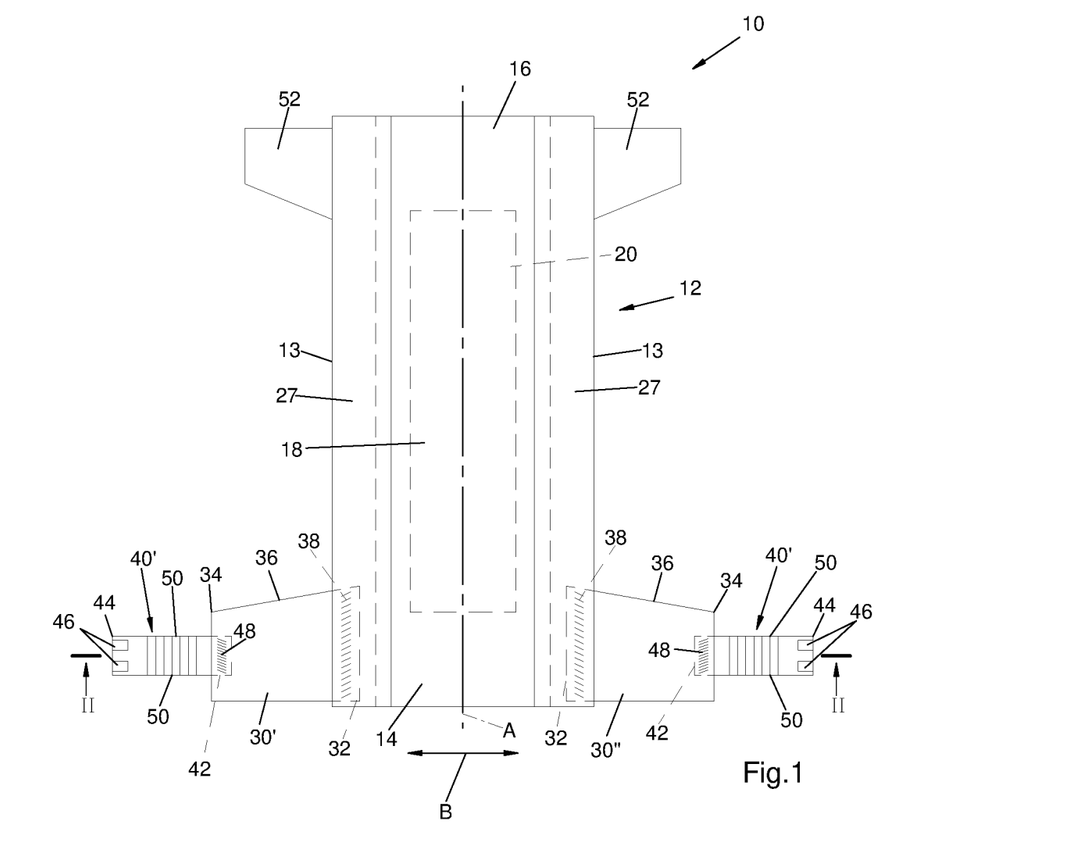
FIG. 1 is a plan schematic view of an absorbent sanitary article in an extended position.

With reference to FIGS. 1-4, numeral 10 indicates an absorbent sanitary article. The absorbent sanitary article 10 comprises a central body 12 or chassis having an elongated shape along a longitudinal axis A. The central body 12 may have a rectangular shape, as illustrated in FIG. 1 with two straight side edges 13 and parallel to the longitudinal axis A. Alternatively, the two side edges 13 may be shaped to conform to the user's legs.

The central body 12 has a rear waist section 14, a front waist section 16 and a crotch section 18 which extends between the rear waist section 14 and the front waist section 16 and which—in use—is arranged between the legs of the user.

Figure 2:
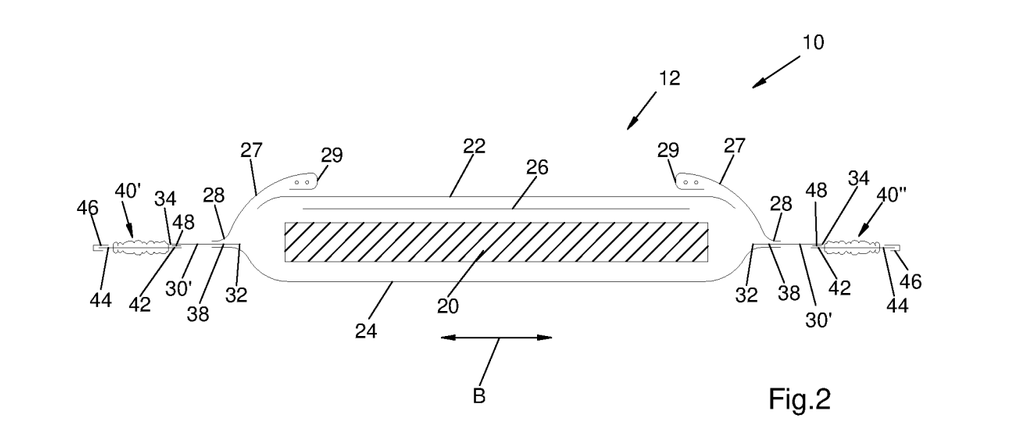
FIG. 2 is a schematic cross-section along the line II-II of FIG. 1.

The central body 12 comprises an absorbent core 20 sandwiched between a liquid-permeable topsheet 22, which faces the wearer's skin in use and a liquid-impermeable backsheet 24, which faces the wearer's clothing in use.

The central body 12 may include an acquisition and distribution layer 26 arranged between the topsheet 22 and the absorbent core 20.

The central body 12 may also comprise two leg cuffs 27, which extend longitudinally on the topsheet 22. Each leg cuff 27 comprises a non-woven strip having an outer edge 28 fixed to a corresponding side edge 13 of the central body 12 and an inner edge 29 in which at least one elastic thread tensioned in the longitudinal direction is arranged, so that—in use—the inner edge 29 of each leg cuff 27 adheres elastically against the user's legs.

The absorbent sanitary article 10 comprises first and second rear side panels 30', 30" which—in the extended configuration of the absorbent sanitary article 10—extend in a transverse direction towards the outside with respect to the central body 12.

The first and second rear side panels 30', 30" have respective proximal edges 32 and respective distal edges 34. The first and second rear side panels 30', 30" may have transverse edges 36 shaped to conform to the user's legs in the condition of use. In possible embodiments, the rear side panels 30 may have a trapezium shape, in which the proximal edges 32 and the distal edges 34 form the major bases and the minor bases of the trapeziums, respectively.

The proximal edges 32 of the first and second rear side panels 30', 30" are fixed to corresponding side edges 13 of the rear waist section 14 of the central body 12. The attachment area between the proximal edges 32 of the first and second rear side panels 30', 30" and the side edges 13 of the rear section 14 is indicated by 38 in FIG. 2.

Figure 3:
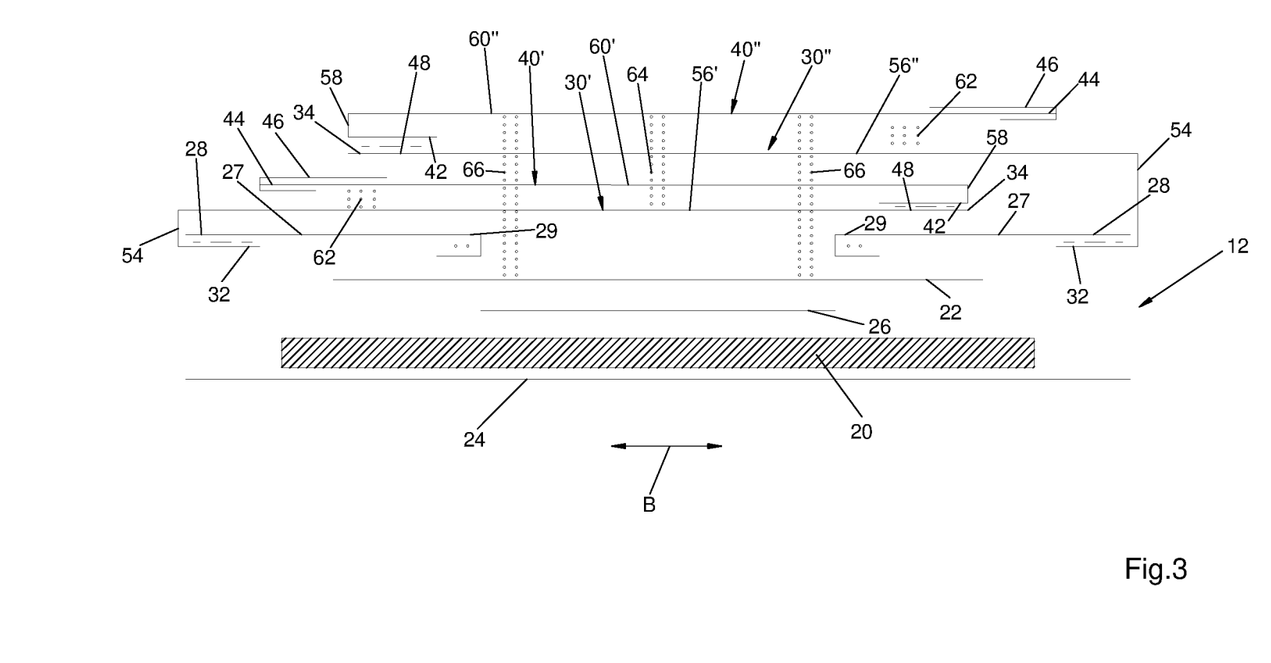
FIG. 3 is a schematic cross-section illustrating a first embodiment of an absorbent sanitary article in an extended configuration.
Figure 4:
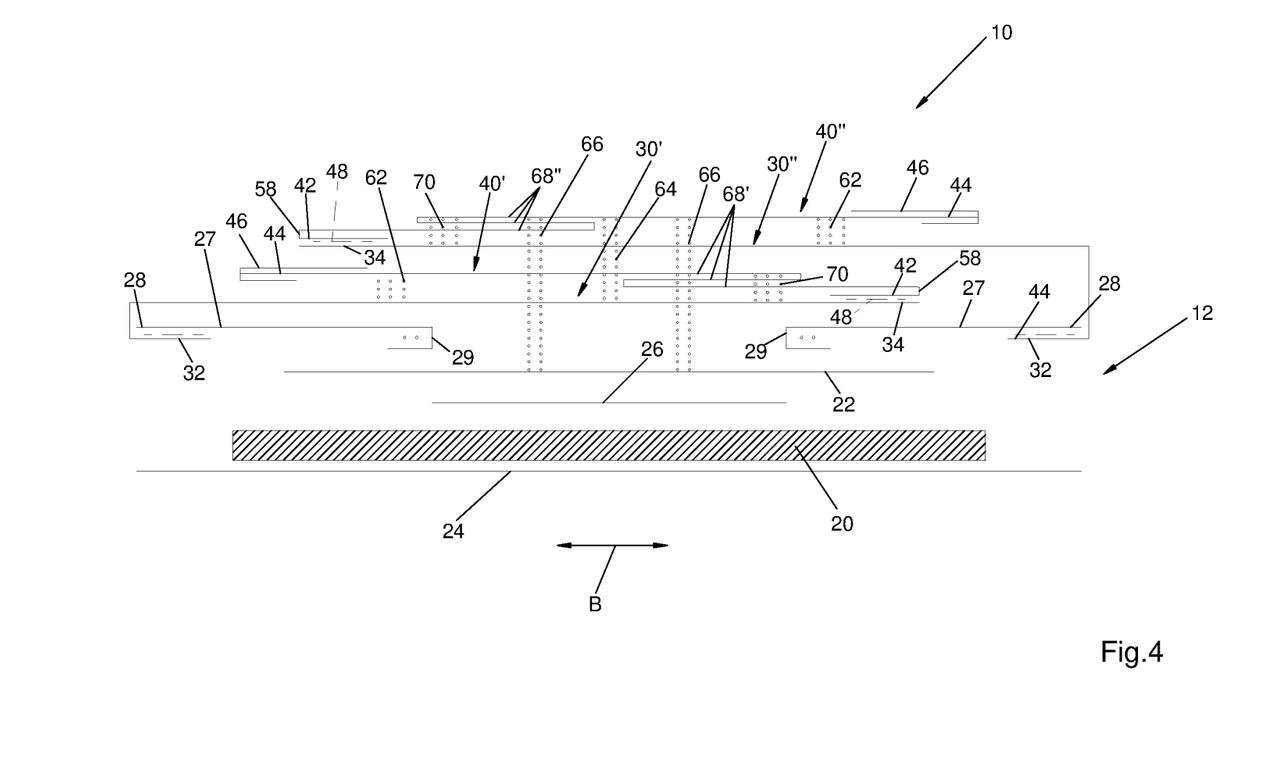
FIG. 4 is a schematic cross-section illustrating a second embodiment of an absorbent sanitary article in an extended configuration.

With reference to FIGS. 3 and 4, in a possible embodiment, the proximal edges 32 of the first and second rear side panels 30', 30" may be fixed between corresponding outer edges of the backsheet 24 and the outer edges 28 of the leg cuffs 27. The fastening may be carried out by welding (for example, thermo-compression or ultrasonic) or by glue.

In a possible embodiment, the proximal edges 32 of the first and second rear side panels 30', 30" may be fixed between corresponding outer edges of the backsheet 24 and of the topsheet 22.

The absorbent sanitary article 10 comprises at least one extension band 40', 40" having a proximal edge 42 fixed to the distal edge 34 of a side panel 30', 30" and a distal edge 44 to which at least one closing element 46 is fixed.

In the embodiment illustrated in the figures, the absorbent sanitary article 10 comprises first and second extension bands 40', 40" having respective proximal edges 42 fixed to respective distal edges 34 of respective first and second side panels 30', 30".

Below, reference will be made to the embodiment in which the absorbent sanitary article 10 comprises two extension bands 40', 40" but it is understood that what is described applies equally to the case wherein the absorbent sanitary article 10 comprises only one extension band 40', 40".

The fastening areas between the proximal edges 42 of the first and second extension bands 40', 40" and the respective distal edges 34 of the side panels 30', 30" are indicated by 48. The fastening of the first and second extension bands 40', 40" to the respective first and second side panels 30', 30" may be carried out by welding, such as, for example, thermo-compression or ultrasonic welding, or by glue.

In a possible embodiment, the first and second rear side panels 30', 30" and the first and second extension bands 40', 40" may be formed of different materials. In a possible embodiment, the first and second rear side panels 30', 30" may be formed of non-elastic material, for example from one or more non-woven layers. In a possible embodiment, the first and second extension bands 40', 40" may be made of elastic material, extensible in a transverse direction B. Each extension band 40', 40" may be formed from an elastic laminate comprising at least one elastic element sandwiched between two non-woven layers. In a resting condition, each of the first and second extension bands 40', 40" may have pleated outer surfaces. The proximal edge 42 and the distal edge 44 of each extension band 40', 40' may be non-elastic.

Each extension band 40', 40" may have the shape of a strip elongated in a transverse direction, with two transverse sides 50 parallel to each other.

The closing elements 46 fixed to the distal ends 44 of the extension bands 40', 40" may be closing elements with micro-hooks or adhesives, which allow a surface closure to be carried out with complementary closing elements to close the sanitary absorbent article 10 around the user's waist.

With reference to FIG. 1, the absorbent sanitary article 10 may comprise a pair of front side panels 52, which in the extended configuration of absorbent sanitary article 10 extend in a transverse direction towards the outside with respect to the central body 12.

The front side panels 52 may be fixed to corresponding side edges 13 of the front section 14 of the central body 12. The front side panels 52 may have outer surfaces configured to establish a surface closure with the closing elements 46. In the case wherein the absorbent sanitary article 10 is not provided with front side panels 52, the closing elements 46 may establish surface closure with an outer surface of the front section 14 of the central body 12. According to a further embodiment, both in the case wherein the absorbent sanitary article 10 is provided with front side panels 52, and in the case wherein the absorbent sanitary article 10 is not provided with front side panels 52, the absorbent sanitary article 10 may be provided with a front panel (frontal tape) fixed centrally on the outer surface of the absorbent sanitary article 10 facing outwards in use, or rather, towards the clothing. According to this further embodiment, the front panel is configured to establish a surface closure with the closing elements 46.

In the extended position, each of the extension bands 40', 40" may have a dimension, at rest, in the transverse direction B of between 100 and 400 mm.

The distance at rest in the transverse direction B between the distal edges 34 of the side panels 30', 30" may be between 600 and 900 mm. Consequently, the overall width at rest in the transverse direction B of the rear waistband of the absorbent sanitary article 10 may be between 800 and 1700 mm.

FIGS. 3 and 4 schematically illustrate two embodiments of an absorbent sanitary article 10 in folded positions. The folded positions illustrated in FIGS. 3 and 4 are the positions in which the absorbent sanitary articles 10 are found at the outlet of a production line, and in the packages in which the absorbent sanitary articles 10 are marketed.

In both embodiments of FIGS. 3 and 4, the first and second side panels 30', 30" and the first and second extension bands 40', 40" are folded over the rear section 14 of the central body.

With reference to FIG. 3, in the folded position, the first and second side panels 30', 30" are folded around respective first fold lines 54 with respect to the respective proximal edges 32 fixed to the central body 12 and have respective first and second panel flaps 56', 56".

The first and second extension bands 40', 40" are folded about respective second fold lines 58 with respect to the respective proximal edges 42 fixed to the respective first and second side panels 30', 30", and have respective first and second band flaps 60', 60" overlapped on respective first and second panel flaps 56', 56".

The first panel flap 56' is overlapped on the topsheet 22 and the leg cuffs 27. The second panel flap 56" is overlapped on the first band flap 60'.

The first and second panel flaps 56', 56" and the first and second band flaps 60', 60" are held in the folded positions by temporary joining zones, which may be released with minimal peel force and without damaging the elements between which they extend. Temporary bonds with these characteristics are well known in the absorbent sanitary article industry and may be formed by light welds (known in the art as "technical welds") or by small amounts of glue.

In a possible embodiment, first temporary joining zones 62 extend between the first and second band flaps 60', 60" and the respective first and second panel flaps 56', 56".

In a possible embodiment, at least one second temporary joining zone 64 extends between the second band flap 60" and the first panel flap 56', through the second panel flap 56" and through the first band flap 60'.

In a possible embodiment, at least one third temporary joining zone 66 extends between the second band flap 60" and the topsheet 22, through the second panel flap 56", through the first band flap 60' and through the first panel flap 56'. In the example illustrated in FIG. 3, two third temporary joining zones 66 are provided located on opposite sides with respect to the longitudinal axis A of the central body 12 of the absorbent sanitary article 10.

A second embodiment of an absorbent sanitary article in a folded configuration is illustrated in FIG. 4. The elements corresponding to those previously described are indicated with the same numerical references. With respect to the embodiment of FIG. 3, the first and second band flaps 60', 60" are further Z-folded, and each of the band flaps 60', 60" has three flap sections 68', 69" overlapped on each other.

Also, in the embodiment of FIG. 4, the first and second panel flaps 56', 56" and the first and second band flaps 60', 60" are held in the folded positions by temporary joining 62, zones 64, 66 as previously described. In addition to the temporary joining zones 62, 64, 66 arranged as described in relation to FIG. 3, in the embodiment of FIG. 4 fourth temporary joining zones 70 may be provided, which extend between the first and second band flaps 60', 60" and the respective first and second panel flaps 56', 56" through the respective flap sections 68', 68" overlapped on each other.

It can be noted that in both embodiments of FIGS. 3 and 4, the closing elements 46 are uncovered and adjacent to the side edges 13 of the central body 12. To open the absorbent sanitary article into the position of use, it is sufficient to grasp the closing elements 46 and pull them in opposite directions outwards. In this way, the temporary joining zones 62, 64, 66, 68, which hold the first and second panel flaps 56', 56" and the first and second band flaps 60', 60" in the folded position yield, and the side panels 30', 30" and the respective first and second extension bands 40', 40" are arranged in the open position shown in FIG. 1.

Despite the considerable extension of the rear waistband in the open position (which can be between 800 and 1700 mm), in the folded configuration the absorbent sanitary article has a width equal to the width of the central body, which may be between 300 and 400 mm.

Figure 5:
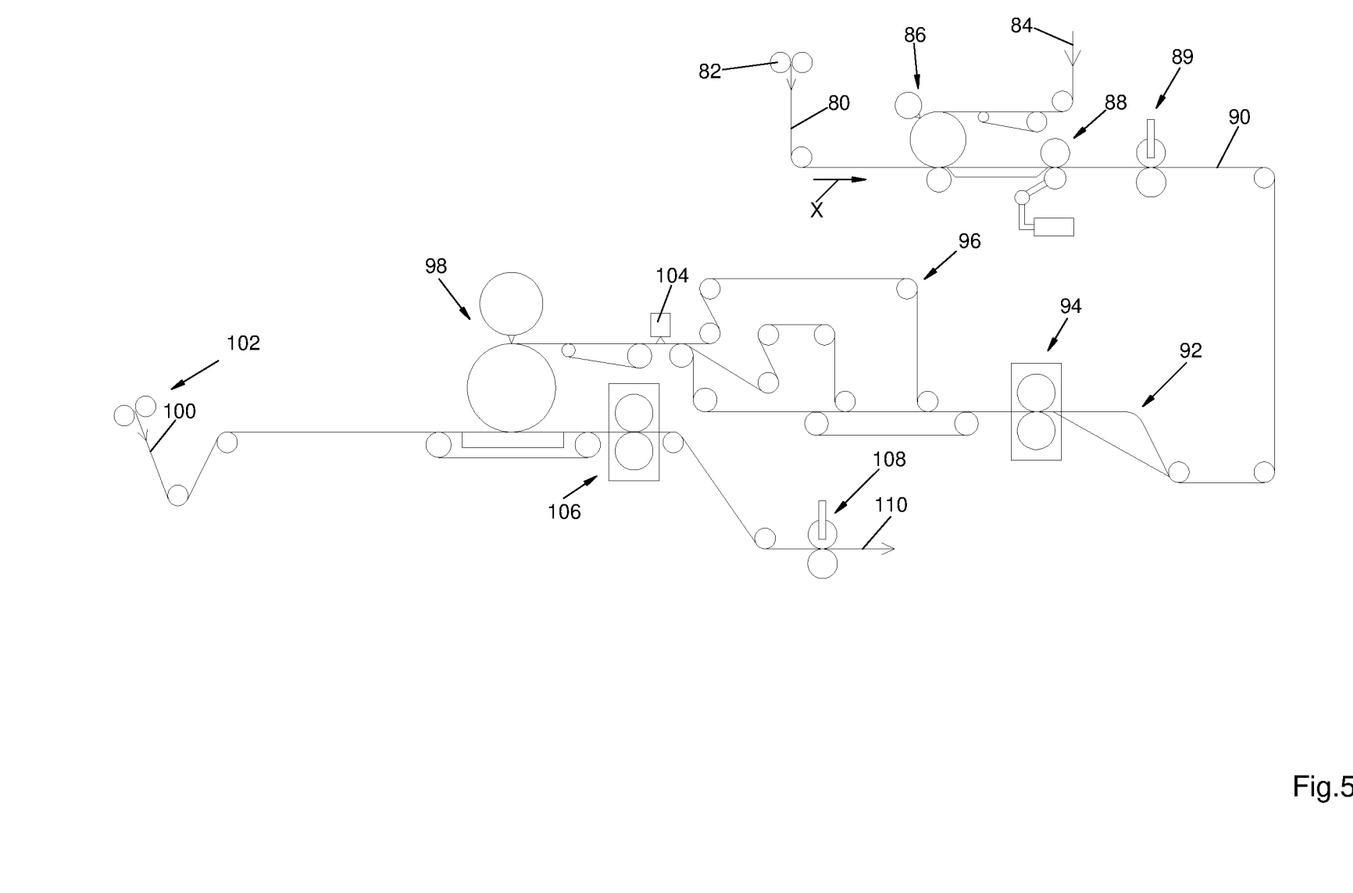
FIGS. 5, 6 and 7 are schematic views illustrating various cross-sections of a method for producing absorbent sanitary articles according to the present invention.
Figure 6:
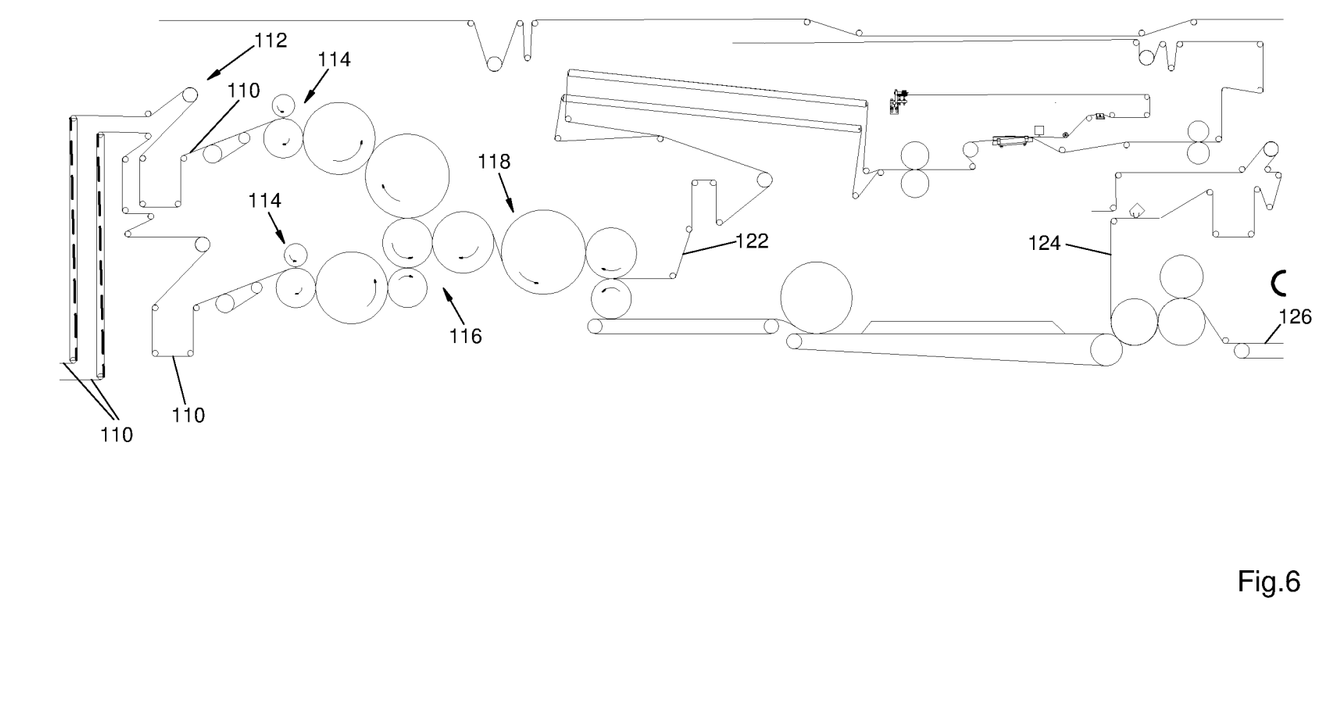
Figure 7:
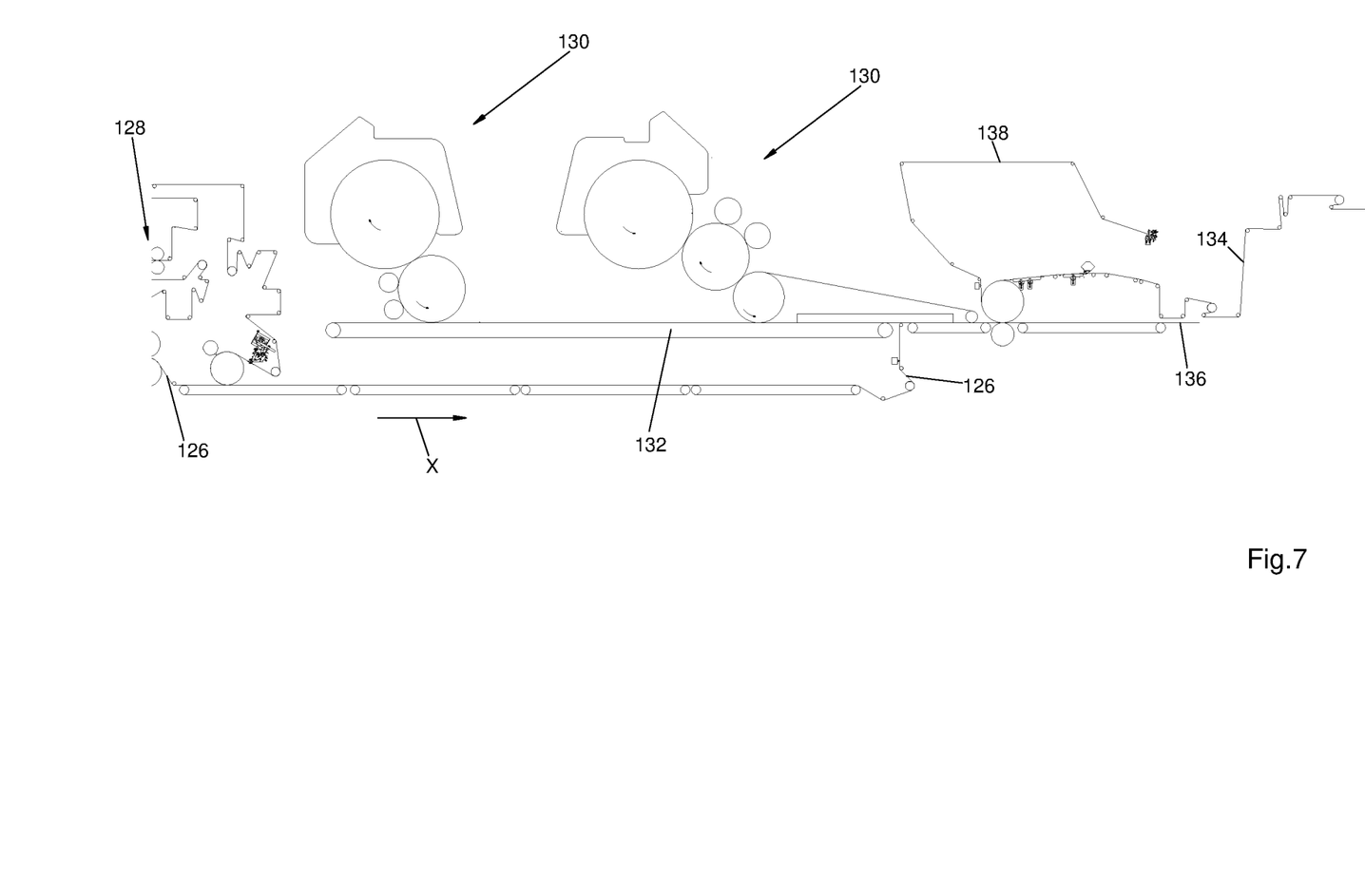

FIGS. 5, 6 and 7 schematically illustrate successive cross-sections of a method for producing absorbent sanitary articles 10 according to the present invention.

With reference to FIG. 5, the method envisages feeding a continuous laminate 80 in the direction of its longitudinal axis X by a first feeding device 82. The continuous laminate 80 may be stretchable elastically in a transverse direction perpendicular to the longitudinal axis X.

A continuous closing tape 84, such as a micro-hook tape, is transversely cut in a first cut-and-slip unit 86 to form a row of closing elements (indicated by 46 in FIGS. 1-4). The first cut-and-slip unit 86 applies the closing elements along the side edges of the continuous laminate 80 in spaced apart positions along the longitudinal axis X. The closing elements may be fixed to the continuous laminate 80 in a first welding unit 88.

Then, the continuous laminate 80 is cut in the longitudinal direction in a first longitudinal cutting unit 89 to form two separate continuous webs 90, each of which has an array of closing elements at an outer edge.

The two continuous webs 90 are folded in the longitudinal direction in a longitudinal folding unit 92 so as to form on each of the two continuous webs 90 a single U-shaped lateral fold (embodiment of FIG. 3) or a U-shaped lateral fold and a central Z-fold (embodiment of FIG. 4).

After having made the folds, the folded flaps of the two continuous webs 90 may be subjected to a compression step carried out in a compression unit 94.

After having made the folds, the two continuous webs 90 may be reversed in a first reversal unit 96, so that after the reversal the two continuous webs 90 have the respective closing elements along their respective edges facing each other.

Subsequently, the two continuous webs 90 are cut transversely in a second cut-and-slip unit 98, so as to form two rows of folded extension bands, indicated with 40', 40" in FIGS. 3 and 4.

The method envisages feeding a continuous web 100 by a second feeding unit 102. The continuous web 100 may be of non-elastic material, for example, of non-woven fabric. The second cut-and-slip unit 98 applies pairs of folded extension bands onto the continuous web 100 at positions spaced apart from each other in the longitudinal direction. The pairs of folded extension bands are fixed to the continuous sheet 100 along respective outer edges. This fastening may be carried out by glue, which can be applied to the two continuous webs 90 upstream of the second cut-and-slip unit 98 by a glue dispensing device 104. Alternatively, the pairs of folded extension bands may be fastened to the continuous web 100 by thermal or ultrasonic welding.

The pairs of folded extension bands fastened along their proximal edges to the continuous web 100 are then joined to the continuous web 100 in a temporary welding unit 106 to form the temporary joining zones indicated by 62 and 70 in FIGS. 3 and 4.

Then, the continuous web 100 is cut in the longitudinal direction in a second longitudinal cutting unit 108 so as to form two separate continuous webs 110, each of which has a respective row of folded extension bands fixed to one of its outer edges and joined to it by temporary joining zones.

With reference to FIG. 6, the two continuous webs 110 may be reversed in a second inversion unit 112, so that after the inversion the two continuous webs 110 have the edges along which the folded extension bands are fixed facing each other.

Then, the two continuous webs 110 are cut in respective cutting units 114 so as to form two rows of side panels, indicated with 30', 30" in FIGS. 1-4, each with a respective folded extension band 40', 40" fixed to one of its edges.

Then, each second side panel 30" with the respective second folded extension band 40" fixed thereto is partially overlapped on a first side panel 30' with the respective first folded extension band 40' fixed thereto. This overlapping may be done on an anvil wheel of a welding unit 116. In the welding unit 116, the first and second side panels 30', 30"

and the respective folded extension bands 40', 40" fixed thereto and overlapped on each other may be subjected to welding operations to form the temporary joining zones 64 (FIGS. 3 and 4), which join together the second band flap 60" and the first panel flap 56' through the second panel flap 56" and through the first band flap 60'.

The array of overlapping side panels thus formed is fed to a repitching unit 118, which spaces apart the side panels in the longitudinal direction.

A leg cuff forming unit 120 forms two continuous strips of leg cuffs 122 provided with respective elastic bands and spaced apart from each other in the transverse direction.

The repitch unit 118 applies the array of side panels overlapped on each other on the two continuous strips of leg cuffs 122. The proximal edges of the first and second side panels 30', 30' may be glued or welded to the respective continuous strips of leg cuffs 122.

Then, a continuous topsheet web 124 is fixed between the two continuous strips of leg cuffs 122 to form a continuous composite web 126 including the continuous strips of leg cuffs 122, the continuous topsheet web 124 and an array of first and second side panels 30', 30" with respective folded extension bands 40', 40".

In a possible embodiment, the proximal edges of the first and second side panels 30', 30" may be fixed by glue or by welding to respective outer edges of the topsheet 22.

With reference to FIG. 7, the continuous composite web 126 is made to advance in the X direction and acquisition and distribution layers may be applied thereon, indicated with 26 in FIGS. 1-4, formed by a unit 128.

At least one forming unit 130 forms absorbent cores, indicated by 20 in FIGS. 1-4, which advance spaced apart in the X direction on a conveyor 132. In the illustrated example, two forming units 130 are provided, which form two rows of overlapped absorbent cores.

The absorbent cores are sandwiched between the continuous composite web 126 and the continuous backsheet web 126 to form a continuous absorbent structure 136. Continuous leg elastic bands 138 may be applied between the continuous composite web 126 and the continuous backsheet web 134.

The side edges of the continuous strips of leg cuffs 122 may be secured to corresponding side edges of the continuous backsheet web 134 so as to fasten the proximal edges 32 of the side panels 30', 30" between the side edges of the continuous strips of leg cuffs 122 and the side edges of the continuous backsheet web 134.

In a possible embodiment, the side edges of the continuous strips of leg cuffs 122 may be fixed to corresponding side edges of the continuous topsheet web 124 and the side edges of the continuous topsheet 124 and backsheet 134 webs may be fixed to each other so as to fix the proximal edges 32 of the side panels 30', 30" between the side edges of the continuous topsheet 124 and backsheet 134 webs.

Then, the continuous absorbent structure 136 is cut to form individual absorbent sanitary articles 10.

Of course, without prejudice to the principle of the invention, the details of construction and the embodiments may vary, even significantly, with respect to those illustrated here, purely by way of non-limiting example, without departing from the scope of the invention as defined by the attached claims.

The invention claimed is:

1. A method for producing absorbent sanitary articles, comprising:
    forming rows of first and second extension bands having respective proximal edges, respective distal edges to which respective closing elements are fixed, and respective first and second band flaps,
    overlapping said first and second extension bands on a continuous web in spaced apart positions in a longitudinal direction and fixing the proximal edges to said continuous web,
    connecting said first and second band flaps to said continuous web by first temporary joining zones,
    cutting said continuous web in the longitudinal direction so as to form two continuous webs separated from each other, each of which has a respective row of first or second extension bands fixed to one of its side edges,
    cutting said continuous webs so as to form pairs of first and second side panels having respective proximal edges and respective distal edges, each with respective first and second extension bands fixed to its the respective distal edges of the side panels,
    overlapping on each other said first and second side panels with the respective first and second extension bands fixed thereto and joining said first and second side panels by second temporary joining zones,
    wherein said first and second extension bands are folded around respective fold lines with respect to the respective proximal edges of the extension bands and have the respective first and second band flaps overlapped on respective first and second panel flaps,
    Z-folding said first and second band flaps so that each of said first and second band flaps has three flap sections overlapped to each other, and forming fourth temporary joining zones between said first and second band flaps and the respective first and second panel flaps extending through respective flap sections overlapping each other,
    fixing the proximal edges of said side panels alongside edges of a continuous composite structure, and
    cutting said continuous composite structure so as to form individual absorbent sanitary articles.

2. The method of claim 1, comprising overlapping said first and second side panels overlapped and joined to each other, to a continuous topsheet of the continuous composite structure and joining said first and second side panels to said continuous topsheet by third temporary joining zones.

3. The method of claim 1, comprising fixing the proximal edges of said first and second side panels to respective side edges of a continuous topsheet web of the continuous composite structure and subsequently fixing said continuous topsheet web to a continuous backsheet web of the continuous composite structure so that the proximal edges of said first and second side panels are fixed between corresponding side edges of the continuous topsheet web and of the continuous backsheet web.

4. The method of claim 1, wherein said first and second side panels are formed of non-elastic material and wherein said first and second extension bands are formed of a material elastically stretchable in a transverse direction.

5. The method of claim 1, comprising cutting said first and second side panels to form respective transverse inclined or shaped edges adapted to conform to a user's legs in a condition of use.

6. A method for producing absorbent sanitary articles, comprising:
    forming rows of first and second extension bands having respective proximal edges, respective distal edges to which respective closing elements are fixed, and respective first and second band flaps,
    overlapping said first and second extension bands on a continuous web in spaced apart positions in a longitudinal direction and fixing the proximal edges along respective side edges to said continuous web, connecting said first and second band flaps to said continuous web, cutting said continuous web in the longitudinal direction so as to form two continuous webs separated from each other, each of which has a respective row of first or second extension bands fixed to one of its side edges, cutting said two continuous webs so as to form pairs of first and second side panels having respective proximal edges and respective distal edges, each with respective first and second extension bands fixed to the respective distal edges of the side panels, fixing the proximal edges of said side panels alongside edges of a continuous composite structure including forming two continuous strips of leg cuffs and fixing the proximal edges of said first and second side panels to respective continuous strips of leg cuffs, and subsequently attaching said continuous strips of leg cuffs to a continuous backsheet of the continuous composite structure so that the proximal edges of said first and second side panels are fixed between corresponding side edges of the continuous backsheet and of the continuous strips of leg cuffs, and cutting said continuous composite structure so as to form individual absorbent sanitary articles.

\* \* \* \* \*